United States Patent [19]

Killion

[11] Patent Number: 4,781,196

[45] Date of Patent: Nov. 1, 1988

[54] CONDUCTIVE EARTIP ASSEMBLY

[75] Inventor: Mead C. Killion, Elk Grove Village, Ill.

[73] Assignee: Etymotic Research, Inc., Elk Grove Village, Ill.

[21] Appl. No.: 17,480

[22] Filed: Feb. 20, 1987

[51] Int. Cl.⁴ .......................... A61B 5/04; A61B 5/12
[52] U.S. Cl. ..................................... 128/642; 128/746
[58] Field of Search .............. 128/642, 746, 640, 641, 128/784–786, 789; 181/129, 130, 135

[56] References Cited

U.S. PATENT DOCUMENTS

| 4,050,453 | 9/1977 | Castillo et al. | 128/640 |
| 4,592,370 | 6/1986 | Lee et al. | 128/746 |
| 4,601,294 | 7/1986 | Danby et al. | 128/642 |
| 4,622,975 | 11/1986 | Danby et al. | 128/642 |

OTHER PUBLICATIONS

Medical Instrumentation, Webster, pp. 245-247, 1978.

*Primary Examiner*—Lee S. Cohen
*Attorney, Agent, or Firm*—Neuman, Williams, Anderson & Olson

[57] ABSTRACT

An eartip electrode constructed of a plastic or vinyl tubular central channel having a soft foam material laterally surrounding the distal end of the channel. Electrical conductivity from the skin of the earcanal is provided by a very thin, soft conductive film coupled to and surrounding the foam material.

9 Claims, 1 Drawing Sheet

CONDUCTIVE EARTIP ASSEMBLY

FIELD OF THE INVENTION

This invention relates to the field of sensory electrodes generally and more specifically to sensory electrodes adapted for contact with the skin.

BACKGROUND OF THE INVENTION

Sensory eartips for measuring an individual's response to auditory stimuli are known in the art. For example, U.S. Pat. No. 4,622,975 dated Nov. 18, 1986 describes an earcanal electrode utilizing a tubular electrode of conductive material having an end area surrounded by plastic foam which is impregnated with a conductive gel for sensing electrical stimuli from the skin of the earcanal that results from the audio stimulus through a sound channel within the electrode. The description of the prior devices and the environment for the apparatus described in the '975 patent is incorporated herein by reference and forms a part of the present disclosure. Eartips of the general type shown in U.S. Pat. No. 4,622,975 are also made by Avonics Instruments of Mountain View, Calif.

Eartips of the foregoing general type have had certain inherent disadvantages. The gels that impregnate the foam generally dry out in normal atmospheric conditions, necessitating the use of expensive, air impervious packaging. Once the integrity of the packaging is compromised, rapid deterioration can be expected. Provision of a separate gel container complicates the use of the eartips by the operator of the diagnostic equipment. Additionally, the use of a metal conductor deep in the earcanal involves inherent risks of injury to the sensitive membranes of the ear by a careless or incompetent diagnostician.

SUMMARY OF THE INVENTION

The present invention has as its principal object the provision of an eartip that is easier to construct and use than those presently on the market.

It is a more specific object to provide an eartip that has no rigid metal parts or surfaces extending into the earcanal and creating a potential hazard to the subject using the device.

It is still a further object to provide an eartip that is economical to manufacture and to package.

Finally, it is an object of the present invention to provide an eartip which has an indefinite shelf life inside or outside of its packaging and which generally overcomes the drawbacks and deficiencies of prior devices of the same general type.

These and other objects and advantages are provided in the present invention through the use of an eartip constructed of a plastic or vinyl (non metallic) tubular central channel having a soft foam material surrounding but not covering the distal open end. Electrical conductivity from the skin of the earcanal is provided by the use of a very thin flexible film of a flexible polymeric material having characteristics such that a thin metal film may be adhered thereto. Such a thin metal film is metal plated on the material by vacuum deposition or the like to provide good electrical conductivity without corresponding mechanical rigidity. Wrapped substantially around the foam end of the eartip and extending up the shank of the tubing, the metallized film provides both a comfortable conductive surface for compression fit within the earcanal and a continuous metallic electrode surface to which any suitable electrical connector, such as an alligator clip or the like, can be attached. No gels, fluids or other metallic parts are necessary.

These and other objects and advantages of the present invention will become more apparent upon reading the following detailed description in conjunction with the associated drawings.

While the invention will be described in connection with certain preferred embodiments, I do not intend that it be limited to those embodiments but rather to include all alternatives, equivalents and variations within the spirit and scope of the invention as defined by the appended claims.

DESCRIPTION OF THE PREFERRED EMBODIMENT

Figure 1:
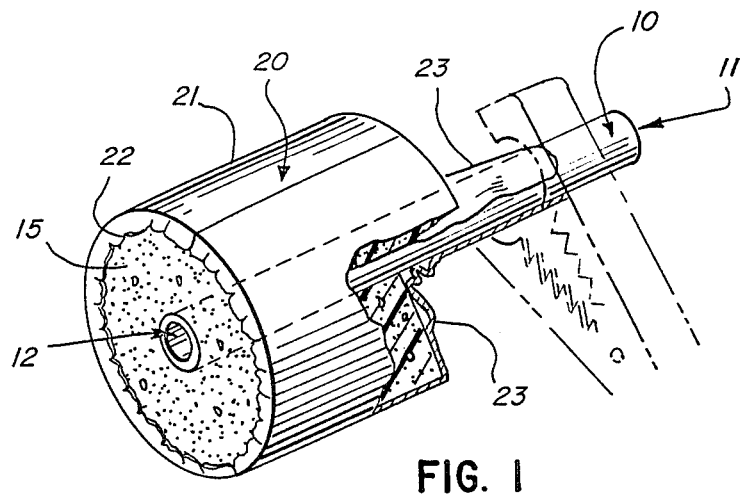
FIG. 1 is a perspective view of an eartip assembly constructed in accordance with the present invention.
Figure 2:
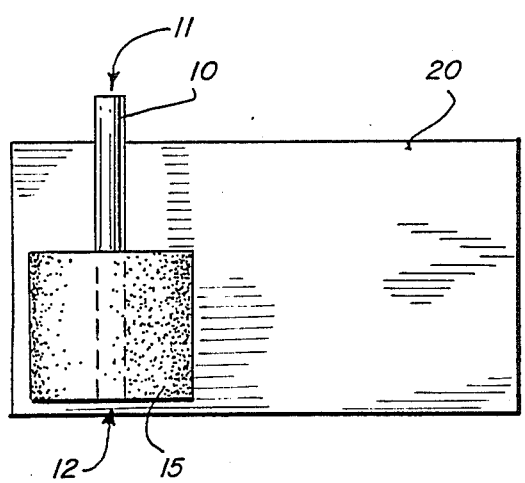
FIG. 2 is a view of a blank of metallized material and the interior foam and tubing components of the present invention in an intermediate stage of assembly.
Figure 3:
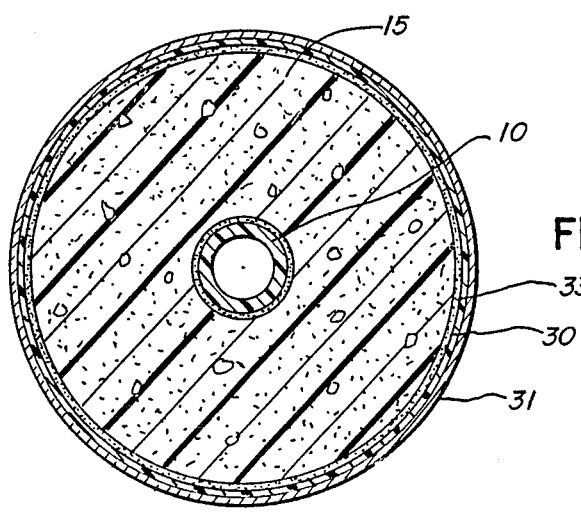
FIG. 3 is a cross-sectional view of the eartip assembly of claim 1 showing the various layers of materials used. The relative thicknesses of the materials are for illustrative purposes only and are in some instances greatly exaggerated.

Turning first to the drawings, FIGS. 1-3 illustrate the principal parts of the invention from different perspectives. The eartip assembly includes a central tubular element 10 which can typically be number 13 vinyl tubing having an inside diameter of 0.076 includes and an outside diameter of approximately 0.109 inches. A wide variety of other materials having generally similar dimensions can also be used. The length of the tubular element 10 is chosen to provide the appropriate acoustical characteristics. A convenient length for transport, packaging and use has been approximately 26 millimeters.

Surrounding the distal end 12 of the tubular element and extending approximately half-way back along the element is a cylindrical wrap or tip portion 15 of soft compressible foam. The foam is generally of the type which is substantially compressible but which has a slow recovery rate from full compression. A detailed description of a suitable material of this type is contained in U.S. Pat. No. Re. 29,487 reissued Dec. 6, 1977, the disclosure of which is incorporated herein by reference and forms a part of this disclosure. As there described, the foam is preferably of vinyl chloride homopolymers and/or copolymers having a diameter in the range of 0.630-0.640 inches and a length of between 0.495 and 0.615 inches, although we have found it preferable to employ a length between 0.45 and 0.55 inches. The foregoing ranges are not critical or essential, however, and the shape and size of the foam tip portion may be varied to provide maximum comfort and ease of entry for any chosen earcanal. The compressibility of the foam assists in establishing the proper pressure on the skin for conductivity to and through the metallic covering which is described below.

The foam 15 and tubular element 10 are preferably bonded together along their concentric mating surfaces using any suitable based adhesive. I have found solvent based adhesives particularly suitable for this purpose.

For the purpose of providing a conductive path for electricity from the skin of the earcanal to the exterior of the ear, the eartip has a conductive metal skin 20 which has a generally cylindrical central portion 21, a slightly crumpled or folded distal end portion 22 and a substantially crumpled frontal end portion 23 extending inward and along the length of the tubular element 10 to provide a convenient means for attachment to suitable exterior electrodes (not shown) that connect to exterior diagnostic equipment for the purposes described in the aforesaid U.S. Pat. No. 4,622,975.

The outer conductive skin or layer 20 is shown in its pre-assembly form in FIG. 2 and in the cross-sectional view of FIG. 3, with the thickness being exaggerated in FIG. 3 to illustrate the combination of layers or elements of which the material is constituted.

In accordance with the present invention, the conductive skin 20 is preferably constructed of a thin polymeric material 30 which has deposited thereon, typically by vacuum deposition, a thin film 31 or conductive metal such as gold. The polymeric material 30 may preferably be a polyethylene terephthalate material or the like, such as a material available under the trademark "Mylar", capable of having a thin metal layer applied and bonded thereto. In a particularly effective embodiment a strip such a polymeric material approximately 1.0 by 2.0 inches and having a thickness of 60 micro inches is vacuum coated with gold to a thickness of approximately 1 micro inches. The uncoated interior surface of the polymeric material 30 is sprayed with an adhesive 33 such as 3M "Super 77 Spray Adhesive" before applying it to the foam material portion 15. At the same time, the film material 30 is thin enough to allow it to crumple at the portion 23 around the shank portion of the tubular element 10 without separation therefrom.

In use, the earplug is simply rolled slowly between the fingertips to allow the covered foam to compress and thereby reduce in diameter. The compressed plug is inserted into the earcanal and allowed to expand slowly, creating a compressive, conductive interface between the skin and the metallic coated layer 3 of the film 20. A thin coating of conductive jell may be used to obtain an even lower-resistance contact to the skin, but is generally not required in a clean earcanal, and the relatively large capacitive coupling obtained from the large-area intimate contact provided herein between the soft conductive film and the earcanal may be sufficient for adequate recordings in many cases. A suitabe clip is coupled to the crumpled end portion 23 of the film 20 to provide an electrical path from the skin of the earcanal to external monitoring equipment. The circuit path is typically closed through a ground connection to the patient at some suitable point on the body. An audio acoustical signal such as a click is delivered to the outer end 11 of the tubular element 10 through a suitable transducer and coupling element (not shown) which mates with the tube end 11 mechanically. A particularly advantageous apparatus for incorporating an eartip of the type disclosed herein is found in applicant's copending patent application Ser. No. 06/628,009 filed July 5, 1984.

The acoustical energy emanating from the distal end 12 of the tubular element 10 excites the neurons in the inner ear and brainstem, causing them to discharge electrically. The resulting electrical potentials available on the skin surface of the earcanal are sensed through the metallized surface 31 of the film 20 for detection by the external measurement apparatus.

From the foregoing, it should be apparent that there has been brought to the art through the present invention an eartip assembly which overcomes most of the drawbacks and deficiencies of the prior art. The device is easier to manufacture, to package, to store and to use than previously known devices of a similar type.

I claim as my invention:

1. A conductive eartip assembly comprising:
    a tubular central acoustical channel having one end adapted for coupling to an acoustic transducer and a distal open end for delivering sound to the ear;
    a generally cylindrical tip portion laterally surrounding the distal end of said channel and extending outward therefrom to define a size and shape which fits snugly within the ear canal; and
    a conductive film coupled to and surrounding said tip portion and having a portion extending therefrom to define an output conductor, said conductive film being adapted to engage and be electrically coupled to the skin of said ear canal and to thereby couple said output conductor to the skin of said ear canal,
    wherein said central channel is vinyl and said cylindrical tip portion is a plastic foam and wherein said tip portion is cemented to said channel with a vinyl based adhesive.

2. An eartip assembly according to claim 1 wherein said plastic foam is compressible and composed of vinyl chloride homopolymers or copolymers.

3. A conductive eartip assembly comprising: a tubular central acoustical channel having one end adapted for coupling to an acoustical transducer and a distal open end for delivering sound to the ear, a tip portion laterally surrounding the distal end of said channel and extending radially outwardly therefrom, a flexible conductive film coupled to and surrounding said tip portion, and output conductor means for effecting an electrical connection to said conductive film, said tip portion being of a resiliently compressible plastic foam material, said conductive film including a portion surrounding and secured to substantially the entire outer surface of said tip portion and being a soft conductive film which lacks mechanical rigidity and which comprises a very thin polymeric material having a very thin conductive metallic layer on its outer surface, said soft conductive film being coupled to said tip portion with an adhesive, said tip portion with said soft conductive film on the outer surface thereof being adapted to be inserted into an ear canal to create a compressive, conductive interface with a large area of intimate contact between said very thin conductive layer and the skin.

4. An eartip assembly according to claim 3 wherein said conductive metallic layer is gold deposited on said polymeric material through vacuum deposition or the like.

5. An eartip assembly according to claim 4 wherein said vacuum deposited gold layer has a thickness of approximately 1 micro inch.

6. An eartip assembly according to claim 3 wherein said polymeric material has a thickness of approximately 60 micro inches.

7. A conductive eartip assembly as defined in claim 3, said conductive film including portions on one end of said tip portion and extending inwardly for coupling to said output conductor means.

8. A conductive eartip assembly as defined in claim 7, said inwardly extending portions of said film being on the end of said tip portion which is opposite said distal end and closest to said output conductor means.

9. A conductive eartip assembly as defined in claim 8, said conductive film further including portions extending axially along the outside of said tubular central acoustical channel to form said output conductor means.

* * * * *